United States Patent [19]

Ohmori et al.

[11] Patent Number: 5,081,149
[45] Date of Patent: Jan. 14, 1992

[54] ANTIHEPATOPATHIC METHOD

[75] Inventors: Shinji Ohmori, Okayama; Kazumi Ogata, Toyonaka; Takahiro Sakaue, Itami, all of Japan

[73] Assignee: Senju Pharmaceutical Co., Ltd., Osaka, Japan

[21] Appl. No.: 588,097

[22] Filed: Sep. 21, 1990

[30] Foreign Application Priority Data

Sep. 29, 1989 [JP] Japan .................. 1-256370

[51] Int. Cl.$^5$ .............................................. A61K 31/24
[52] U.S. Cl. .................................................... 514/534
[58] Field of Search ........................................ 514/534

[56] References Cited

FOREIGN PATENT DOCUMENTS 63-8337  1/1988  Japan .
2-255624 10/1990 Japan .
3-48626  3/1991  Japan .

OTHER PUBLICATIONS

Calam et al., Biochem. J., 86, 226 (1963).

*Primary Examiner*—Stanley J. Friedman
*Attorney, Agent, or Firm*—Wenderoth, Lind & Ponack

[57] ABSTRACT

The present invention relates to a useful antihepatopathic composition comprising a compound of the formula:

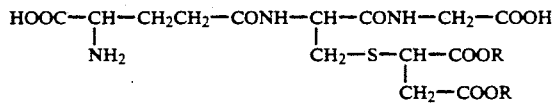

(wherein the R groups are the same or different and each means a hydrogen atom or a lower alkyl group) or a pharmaceutically acceptable salt thereof as an active ingredient.

1 Claim, No Drawings

ANTIHEPATOPATHIC METHOD

BACKGROUND OF THE INVENTION

1. Field of the Invention

This invention relates to an antihepatopathic agent. More particularly, it relates to a useful pharmaceutical composition for the prevention and treatment of hepatopathy which contains S-($\alpha,\beta$-dicarboxyethyl)glutathione which is found in the mammalian body, or an ester derivatives thereof, either in the free form or in a pharmaceutically acceptable salt form.

2. Description of the Prior Art

Many of the antihepatopathic agents so far used contain the group SH. Cysteine and glutathione are typical examples. However, while these agents produce a detoxicating effect owing to their active SH group, they have a disadvantage in that the active SH group reduces the efficacy of a drug or drugs used concomitantly.

The present inventors made intensive investigations in search of potent antihepatopathic compounds having no active SH group, hence having no such disadvantage as mentioned above and, as a result, found that S-($\alpha,\beta$-dicarboxyethyl)glutathione, which is a substance present in the mammalian body, and ester derivatives thereof unexpectedly have very potent antihepatopathic activity and at the same time have a high level of safety. The present invention has been accomplished on the basis of the above findings.

SUMMARY OF THE INVENTION

The invention provides an antihepatopathic composition, namely a pharmaceutical composition for the prevention and treatment of hepatopathy which comprises, as an active ingredient, a compound of the formula

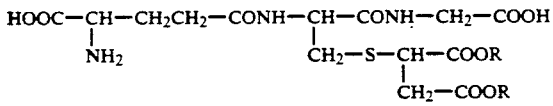

(wherein the two R groups are the same or different and each is a hydrogen atom or a lower alkyl group) or a pharmacologically acceptable salt thereof.

DETAILED DESCRIPTION OF THE INVENTION

Among the active ingredients to be used in the composition according to the invention, S-($\alpha,\beta$-dicarboxyethyl)glutathione is a physiological substance discovered in the bovine crystalline lens by D. H. Calam and S. G. Waley [Biochem. J., 86, 226 (1963)]. At present, however, only a little is known about its pharmacological features. The present inventors have previously found that this compound has blood coagulation inhibiting and platelet aggregation inhibiting activities as well as antiinflammatory and/or antiallergic activity [Japanese Published Unexamined Patent Application (Kokai) No. 63-8337 and Japanese Patent Applications Nos. 1-79956 and 1-183484].

In the above formula, the two R groups are the same or different and each is a hydrogen atom or a lower alkyl group preferably containing 1 to 10 carbon atoms. The carbon chain in said alkyl group may be straight or branched or cyclic. Furthermore, said chain may contain a cyclic portion. Thus, as the alkyl group, there may be mentioned, among others, methyl, ethyl, n-propyl, isopropyl, cyclopropyl, n-butyl, tert-butyl, sec-butyl, n-pentyl, 1-ethylpropyl, isopentyl and benzyl.

In the antihepatopathic composition according to the invention, the active ingredient compound may be in its free form or in the form of a pharmacologically acceptable nontoxic salt, for example an alkali metal salt, such as a sodium salt or potassium salt, or an alkaline earth metal salt, such as a calcium salt or magnesium salt. In cases where said compound is in a salt form, the carboxyl groups occurring in said compound may be either fully or partially involved in salt formation. Any of the possible salts can be used for preparing the composition according to the invention.

The antihepatopathic composition according to the invention may contain one of or a combination of two or more of the active ingredient compounds defined hereinabove, depending on the intended purpose and/or necessity.

The active ingredient compounds to be used in the antihepatopathic composition according to the invention can be produced by various means, for example in the following manner. Thus, S-($\alpha,\beta$-dicarboxyethyl)glutathione can be extracted, isolated and purified from yeasts or the bovine crystalline lens, for instance, since it occurs there. Alternatively, S-($\alpha,\beta$-dicarboxyethyl)glutathione can be synthesized by allowing an equimolar mixture of the starting materials glutathione and maleic acid in aqueous solution or in alcoholic aqueous solution to stand with warming or at room temperature for 1 to 2 days. The use of a maleic acid monoester or diester in lieu of maleic acid gives the corresponding S-($\alpha,\beta$-dicarboxyethyl)glutathione ester derivative. While the compounds synthesized in the above manner have a newly introduced asymmetric carbon atom in their molecules and hence involve optical isomers, both isomers as well as mixtures thereof can suitably be used in the practice of the invention.

The active compound to be used in the antihepatopathic composition of the present invention is a substance present in the body or an ester derivative thereof and therefore it is clear to be scarcely toxic, as evidenced by the data generated and shown in Test Example 2 which is described herein, hence is excellent in safety and can be advantageously used in various dosage forms against various hepatic disorders.

The antihepatopathic composition of the present invention effectively inhibits the onset of liver damage, whether acute or chronic, and prevents elevation of GOT, GPT and LDH values. It is, thus, of value in the prevention and treatment of acute or chronic hepatitis. It can also be used effectively for hepatocirrhosis. The antihepatopathic composition according to the invention controls the fall in liver TG as resulting from ingestion of alcohol and therefore is useful in the prevention and treatment of alcoholic liver disease as well. Furthermore, it can be used advantageously against drug-induced liver damage, for example the damage caused by acetaminophen.

In the prevention and/or treatment of various forms of hepatopathy, such as those mentioned above, the composition according to the invention is suitably applied either orally or parenterally depending on the disease to be treated. Usable dosage forms are, for instance, solid form preparations, such as tablets, granules, powders and capsules, and liquid form preparations such as injections. These preparations can be prepared by methods well known in the art. The preparations may contain, as necessary, those inert components, auxiliaries and additives that are commonly used in the pharmaceutical practice, for example binders, disintegrants, thickeners, dispersants, reabsorption promoting agents, corrigents, flavors, buffers, surfactants, solubilizers, preservatives, emulsifiers, isotonizing agents, stabilizers and pH adjusting agents, each in an appropriate amount.

The dose of the active ingredient compound mentioned above may vary depending on the compound, patient's age and body weight, dosage form, symptom to be treated and other factors. Generally, however, it is recommendable that, in the case of an injection, for instance, about 10 to 500 mg be administered once daily to each adult human; in the case of peroral dosage forms, about 10 to 1,000 mg be administered several times daily to each adult.

The composition according to the invention may further contain another or other antihepatothic agents and/or another or other agents capable of producing other pharmacological effects unless the object of the invention becomes unattainable.

The following examples are further illustrative of the present invention.

TEST EXAMPLE 1

Test for pharmacological effects on hepatopathy

Method

After 24 hours of fasting, SD-strain male rats weighing 180 g were orally given 200, 400 or 800 mg/kg of S-($\alpha$, $\beta$-dicarboxyethyl)glutathione (hereinafter referred to as "DCE-GS" for short). A control group was given physiological saline. An hour later, 300 mg/kg acetaminophen was intraperitoneally administered to each rat for causing hepatopathy. Twenty-four hours after acetaminophen administration, blood samples were collected from the rats under pentobarbital anesthesia via the abdominal aorta and subjected to blood biochemistry tests. The results obtained are shown below in Table I.

TABLE I

| Test substance | Effects of DCE-GS on acetaminophen-induced hepatopathy in rats | | | | |
|---|---|---|---|---|---|
| | Dose (mg/kg) | s-GOT | s-GPT | LDH | s-TG |
| physiological saline | — | 2545 ± 769 | 1289 ± 339 | 12467 ± 3002 | 27.3 ± 2.3 |
| DCE-GS | 200 | 1221 ± 179 | 499 ± 66 | 6029 ± 485 | 28.8 ± 5.0 |
| | 400 | 677 ± 219* | 262 ± 89* | 4873 ± 973* | 36.1 ± 7.6 |
| | 800 | 438 ± 131* | 133 ± 39* | 3722 ± 595* | 53.9 ± 10.4* |

Each value indicate the mean ± standard error (n = 6 to 8).
Significance level relative to physiological saline: *p < 0.05.
Units are IU/liter for s-GOT and s-GPT; Wrobrewski units for LDH (lactate dehydrogenase); and mg/dl for s-TG (serum triglyceride).

Results

Administration of acetaminophen to rats induced hepatopathy; the s-GOT, s-GPT and s-LDH values increased and the s-TG value decreased.

DCE-GS dose-dependently suppressed the increases in s-GOT, s-GPT and s-LDH as well as the decrease in s-TG.

TEST EXAMPLE 2

Acute toxicity testing by intravenous administration

Acute toxicity testing was carried out by intravenous administration of DCE-GS to groups of 5 male ddy strain mice weighing about 20 g. The doses used were 100, 200, 400, 800 and 1,600 mg/kg (common ratio=2). The injection were adjusted to pH 7 with 1N sodium hydroxide. Neither deaths nor behavioral abnormalities were noted during 72 hours of observation.

SYNTHESIS EXAMPLE 1

S-($\alpha$, $\beta$-Dicarboxyethyl)glutathione

Glutathione (9.2 g) and 5.0 g of maleic acid are dissolved in 150 ml of water and the solution is allowed to stand at room temperature for 12 hours. The reaction mixture is sampled (one or two drops) and one drop of 0.01N $I_2$ test solution is added to the sample. After confirming, in this manner, that there is no more iodine consumption, 6.6 g of copper acetate (monohydrate) is added to the reaction mixture. If a precipitate, which is small in amount, is found, the precipitate is filtered off. The filtrate is concentrated to about 70 ml, ethanol is added to the concentrate, and the resulting blue copper salt precipitate is collected by filtration. This is recrystallized from water-ethanol. This copper salt is further dissolved in 200 ml of water, hydrogen sulfide is passed through the solution to cause precipitation of copper sulfide, and the precipitate is filtered off. The filtrate is concentrated under reduced pressure and ethanol is added to the residue, whereupon white crystals appear. The crystals are collected by filtration, washed with ethanol and recrystallized from water-ethanol to give about 9 g of the desired compound as white amorphous crystals (hygroscopic).

SYNTHESIS EXAMPLE 2

Sodium salt of S-($\alpha$, $\beta$-dicarboxyethyl)glutathione

S-($\alpha$, $\beta$-Dicarboxyethyl)glutathione (2 g) is dissolved in 40 ml of water, the solution is adjusted to pH 7 with 1N NaOH and then concentrated under reduced pressure at a temperature not exceeding 30° C. Ethanol is added to the concentrate and the resulting white crystals are collected by filtration and recrystallized from water-ethanol to give 2.1 g of the desired compound as a white crystalline powder.

SYNTHESIS EXAMPLE 3

Calcium salt of S-($\alpha$, $\beta$-dicarboxyethyl)glutathione

S-($\alpha$, $\beta$-Dicarboxyethyl)glutathione (2 g) is dissolved in 40 ml of water, 1 g of calcium carbonate is added to the solution, and the mixture is stirred with warming. When carbon dioxide gas evolution is no more observed, the excess of calcium is filtered off. The filtrate is concentrated under reduced pressure. Ethanol is added to the concentrate and the resulting white crystalline precipitate is collected by filtration and recrystallized from water-ethanol to give 2.2 g of the desired compound as a white crystalline powder.

SYNTHESIS EXAMPLE 4

Magnesium salt of S-(α, β-dicarboxyethyl)glutathione

S-(α, β-Dicarboxyethyl)glutathione (2 g) is treated with 1 g of basic magnesium carbonate in the same manner as mentioned above for the production of the calcium salt, to give 2.2 g of the magnesium salt.

SYNTHESIS EXAMPLE 5

Sodium salt of S-(diethyl-α, β-dicarboxyethyl)glutathione

Glutathione (9.2 g) and 5.6 g of diethyl maleate are dissolved in 150 ml of 30% (v/v) ethanol. The solution is adjusted to pH 6 with 2N sodium hydroxide and then stirred at 50° C. for about 5 hours. The reaction mixture is sampled (two drops) and one drop of 0.01N iodine test solution is added to the sample. When the color of iodine does not fade any more, gaseous hydrogen sulfide is passed through the reaction mixture. The mixture is allowed to stand overnight and then concentrated, whereby the hydrogen sulfide gas is distilled off. Water (150 ml) is added to the residue for dissolution of the residue. Copper acetate monohydrate (6.6 g) is added to and dissolved in the solution. The copper salt gradually precipitates out. The precipitate is collected by filtration, washed with water and suspended in 150 ml of water. Gaseous hydrogen sulfide is passed through the suspension with stirring for the formulation of copper sulfide. The copper sulfide is filtered off, the filtrate is concentrated, ethanol (200 ml) was added to the residue for dissolving the same, and the solution is adjusted to pH 6 by gradually adding an ethanolic sodium hydroxide solution, whereupon white crystals precipitate out. These are collected by filtration, washed with ethanol and dissolved in water for recrystallization. The solution is concentrated as far as possible and then ethanol is added. The resulting crystalline precipitate is collected by filtration and dried to give 8.5 g of S-diethyl-α, β-dicarboxyethyl)glutathione sodium salt. TLC on silica gel: $Rf=0.28$ (n-butanol-acetic acid-water=4:1:1).

SYNTHESIS EXAMPLE 6

Sodium salt of S-di-n-butyl-α, β-dicarboxyethyl)glutathione

Glutathione (9.2 g) and 7.5 g of di-n-butyl maleate are dissolved in 150 ml of 50% (v/v) ethanol and the reaction is carried out in the same manner as Synthesis Example 5. The solvent is then distilled off and the residue is dissolved in 150 ml of water. Addition of 200 ml of 3.3% aqueous copper acetate to the solution results in precipitation of the water-insoluble copper salt. The precipitate is collected by filtration, washed with water and suspended in 300 ml of 50% (v/v) ethanol. Hydrogen sulfide is passed through the suspension with stirring for the formation of copper sulfide. The copper sulfide is filtered off, the filtrate is concentrated for the removal of hydrogen sulfide. The concentration is dissolved again in 150 ml of 50% (v/v) ethanol, and the solution is adjusted to a pH of about 6 by addition of 2N sodium hydroxide solution and then concentrated. Ethanol, acetone and isopropyl ether are added to the concentrate. The resulting white crystalline precipitate is collected by filtration, washed with acetone and dried to give 9.7 g of S-(di-n-butyl-α,β-dicarboxyethyl)-glutathione sodium salt as hygroscopic crystals. TLC on silica gel: $Rf=0.40$ (n-butanol-acetic acid-water=4:1:1).

SYNTHESIS EXAMPLE 7

Calcium salt of S-(di-n-butyl-α,β-dicarboxyethyl)glutathione

The procedure of Synthesis Example 6 was followed using calcium carbonate in lieu of the 2N sodium hydroxide. Addition of acetone to the concentration residue gives white crystals. They are recrystallized from ethanol-acetone to give 7.5 g of S-(di-n-butyl-α, β-dicarboxyethyl)glutathione calcium salt.

SYNTHESIS EXAMPLE 8

Sodium salt of S-(monoethyl-α,β-dicarboxyethyl)glutathione

Glutathione (9.2 g) and 4.5 g of monoethyl maleate are dissolved in 150 ml of water, the solution is adjusted to pH 6.0 with 2N sodium hydroxide, and the reaction is carried out in the same manner as Synthesis Example 5. The reaction mixture is concentrated, ethanol is added to the residue, and the resulting precipitate white crystals are collected by filtration and dissolved in water for recrystallization. The aqueous solution is concentrated and ethanol is added to cause crystallization. Yield 8.0 g. TLC on silica gel: $Rf=0.17$ (n-butanol-acetic acid-water=4:1:1).

DOSAGE FORM EXAMPLE 1

| Peroral tablets | |
| --- | --- |
| DCE-GS calcium salt | 100 mg |
| Lactose | 80 mg |
| Starch | 17 mg |
| Magnesium stearate | 3 mg |

Tablets are produced by a conventional method using the above materials, the quantities given above being for one tablet. The tablets may be sugar-coated as necessary.

DOSAGE FORM EXAMPLE 2

| Injectable solution | |
| --- | --- |
| DCE-GS sodium salt | 2.5 mg |
| Sodium chloride | 0.6 mg |
| Distilled water for injection | 100 ml |

The above ingredients are mixed up and sterilized by bacterial filtration. The filtrate is distributed in 2-ml portions into glass ampoules and the ampoules are sealed.

What is claimed is:

1. A method for the treatment of hepatopathy which comprises administering to a human in need of such treatment an anti-hepatopathy effective amount of a compound of the formula:

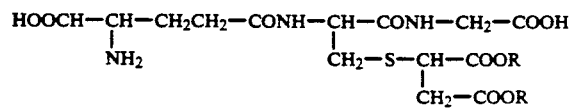

wherein the R groups are the same or different and each means a hydrogen atom or a lower alkyl group or a pharmaceutically acceptable salt thereof as an active ingredient.

* * * * *